US012220598B2

(12) United States Patent
Scurtescu

(10) Patent No.: US 12,220,598 B2
(45) Date of Patent: Feb. 11, 2025

(54) MOUTHPIECE APPARATUS FOR INTRAORAL THERAPY AND RELATED SYSTEM AND METHOD

(71) Applicant: SmileSonica, Inc., Edmonton (CA)

(72) Inventor: Cristian Scurtescu, Edmonton (CA)

(73) Assignee: SmileSonica, Inc., Edmonton (CA)

( * ) Notice: Subject to any disclaimer, the term of this patent is extended or adjusted under 35 U.S.C. 154(b) by 876 days.

(21) Appl. No.: 17/166,898

(22) PCT Filed: Sep. 4, 2019

(86) PCT No.: PCT/CA2019/051234
§ 371 (c)(1),
(2) Date: Feb. 3, 2021

(87) PCT Pub. No.: WO2020/047659
PCT Pub. Date: Mar. 12, 2020

(65) Prior Publication Data
US 2021/0353956 A1  Nov. 18, 2021

Related U.S. Application Data

(60) Provisional application No. 62/727,520, filed on Sep. 5, 2018.

(51) Int. Cl.
*A61N 7/00* (2006.01)
*A61N 5/06* (2006.01)

(52) U.S. Cl.
CPC ........ *A61N 5/0603* (2013.01); *A61N 5/0613* (2013.01); *A61N 5/0624* (2013.01);
(Continued)

(58) Field of Classification Search
CPC ............... A61N 5/0603; A61N 7/00; A61N 2005/0606; A61N 2005/0651;
(Continued)

(56) References Cited

U.S. PATENT DOCUMENTS

2011/0291031 A1   12/2011   Johnson et al.
2016/0331577 A1   11/2016   Thornton
(Continued)

FOREIGN PATENT DOCUMENTS

GB    2475623 A    *  5/2011   ............. A61C 19/06
TW    M376274 U       3/2010

OTHER PUBLICATIONS

Extended European Search Report/PCTCA2019051234/EP19858109.2, Sep. 21, 2021.
(Continued)

*Primary Examiner* — Cris L. Rodriguez
*Assistant Examiner* — Luis Ruiz Martin
(74) *Attorney, Agent, or Firm* — Russell Manning; FisherBroyles, LLP

(57) ABSTRACT

Adjustable mouthpiece apparatuses for intraoral therapy are provided. The mouthpiece apparatus may comprise at least one emitting element to emit at least one therapeutic emission. In some embodiments, the mouthpiece apparatus comprises an upper panel and a lower panel and at least one adjustable connector interconnecting the upper panel and the lower panel and adjustable to change the spacing between the upper panel and the lower panel. The mouthpiece apparatus may thereby be adjusted for a range of vestibular heights. Also provided are related systems including adjustable mouthpiece apparatuses and related methods for making an adjustable mouthpiece apparatus.

15 Claims, 9 Drawing Sheets

(52) U.S. Cl.
CPC ............... *A61N 2005/0606* (2013.01); *A61N 2005/0651* (2013.01); *A61N 7/00* (2013.01)

(58) Field of Classification Search
CPC ...... A61N 5/0613; A61N 5/0624; A61C 7/08; A61C 9/00; A61C 9/0006; A61C 17/0211; A61C 19/05; A61C 19/063; A61C 19/066; A61C 7/36; A61C 5/90; A61C 19/06; A63B 71/085; A63B 23/032; A63B 2071/086; A63B 2071/088; A61F 5/56; A61F 5/58; A61F 2005/563; A61F 5/566
USPC ........................ 433/29, 41, 38, 37; 128/848
See application file for complete search history.

(56) References Cited

U.S. PATENT DOCUMENTS

| 2017/0080249 | A1* | 3/2017 | Brawn | A61N 5/0603 |
| 2019/0358009 | A1* | 11/2019 | Vermeulen | A61C 19/066 |
| 2020/0330753 | A1 | 10/2020 | Leonhardt | |

OTHER PUBLICATIONS

International Search Report PCT/CA2019/051234.
Notification and Transmittal of International Search Report Dec. 12, 2019 PCT/CA2019/151234.

* cited by examiner

MOUTHPIECE APPARATUS FOR INTRAORAL THERAPY AND RELATED SYSTEM AND METHOD

RELATED APPLICATION

This application claims priority to U.S. Provisional Patent Application No. 62/727,520, filed Sep. 5, 2018, the entire contents of which are incorporated herein by reference.

TECHNICAL FIELD

The present disclosure relates to dental apparatuses. More particularly, the present disclosure relates to mouthpiece apparatuses for intraoral therapy and related systems and methods.

BACKGROUND

Intraoral therapy devices may be used to deliver therapeutic emissions, such as ultrasound, light, heat, etc., to the roots of a patient's teeth as well as the bone and tissues supporting and surrounding the roots of the teeth. Such devices may include a mouthpiece that is received into the mouth of the patient to bring at least one emitting element in close proximity to the roots of the teeth and/or alveolar bone.

Mouth anatomy may vary significantly from person to person. The vestibule of the mouth is the area between the teeth, lips, and cheeks, and the height of the vestibule may vary from person to person. For example, larger mouths may have a total vestibular height of approximately 55 mm, while smaller mouths may have a total vestibular height of approximately 35 mm or even 25 mm for very small mouths. In addition, the width of the upper and lower dental arches, i.e. the crescent-like arrangements of teeth within the upper and lower jaws, may also vary significantly between different people.

Conventional mouthpieces may only come in a single size and may therefore only be adapted for a single vestibular height, which may cause discomfort in patients with vestibular heights that are taller or shorter than the height of the mouthpiece. In addition, the mouthpiece may not be optimally positioned to provide therapy to the teeth roots and other target tissues of all users.

SUMMARY

In one aspect, there is provided a mouthpiece apparatus comprising: an upper panel to be positioned proximate a user's maxillary teeth; a lower panel to be positioned proximate the user's mandible teeth; at least one adjustable connector interconnecting the upper panel and the lower panel and adjustable to change a spacing between the upper panel and the lower panel; and wherein at least one of the upper panel and the lower panel comprises at least one emitting element.

In some embodiments, the at least one adjustable connector is compressible and compression of the adjustable connector reduces the spacing between the upper panel and the lower panel.

In some embodiments, the upper and lower panels are approximately parallel.

In some embodiments, each of the upper panel and the lower panel comprises a respective first end and a respective opposed second end and wherein the at least one adjustable connector comprises a first adjustable connector proximate the first ends of the upper and lower panels and a second adjustable connector proximate the second ends of the upper and lower panels.

In some embodiments, each of the first adjustable connector and the second adjustable connector are approximately symmetrical.

In some embodiments, the at least one adjustable connector is approximately S-shaped.

In some embodiments, the at least one adjustable connector comprises: a substantially vertical upper segment extending from the upper panel; a substantially vertical lower segment extending from the lower panel, the lower segment horizontally offset from the upper segment; and a middle segment interconnecting the upper segment and the lower segment.

In some embodiments, the at least one adjustable connector comprises a central adjustable connector approximately midway between the first ends and second ends of the upper and lower panels.

In some embodiments, a bite plate between the upper panel and the lower panel.

In some embodiments, the central adjustable connector comprises an upper portion interconnecting the upper panel to the bite plate and a lower portion interconnecting the bite plate to the lower panel.

In some embodiments, the at least one adjustable connector comprises a flexible resilient material.

In some embodiments, the at least one adjustable connector comprises a plastically deformable material.

In some embodiments, at least one of the upper panel and the lower panel comprises a first portion and a second portion, wherein the first portion and the second portion are interconnected by a flexible connection.

In some embodiments, the at least one emitting element is encapsulated in a flexible casing.

In some embodiments, the flexible casing comprises at least one depression proximate the at least one emitting element.

In some embodiments, the at least one emitting element comprises at least one of an ultrasound emitter, a light emitter, a heat emitter, a vibration emitter, or an electromagnetic field emitter.

In some embodiments, the mouthpiece apparatus further comprises at least one flexible circuit board operatively connected to the at least one emitting element.

In some embodiments, at least a portion of the at least one flexible circuit board is disposed within the at least one adjustable connector.

In another aspect, there is provided a system for intraoral therapy comprising: embodiments of the mouthpiece apparatus described herein and an electronics controller operatively connected to the at least one emitting element to control emissions from the at least one emitting element.

In another aspect, there is provided a method for making a mouthpiece apparatus for intraoral therapy comprising: providing an upper panel and a lower panel; and interconnecting the upper panel and the lower panel with at least one adjustable connector.

In some embodiments, the method further comprises encapsulating each of the upper panel and the lower panel in a respective flexible casing.

In some embodiments, interconnecting the upper panel and the lower panel comprises integrally forming the flexible casings and the at least one adjustable connector.

In some embodiments, the method further comprises providing a bite plate core.

In some embodiments, interconnecting the upper panel and the lower panel comprises: connecting the upper panel and the lower panel to the bite plate core to form a panel/core assembly; securing the panel/core assembly using a first portion of flexible resilient material; and forming the at least one adjustable connector and encapsulating the secured panel/core assembly in a flexible casing using a second portion of flexible resilient material.

Other aspects and features of the present disclosure will become apparent, to those ordinarily skilled in the art, upon review of the following description of the specific embodiments of the disclosure.

DETAILED DESCRIPTION OF EMBODIMENTS

Generally, the present disclosure provides an adjustable mouthpiece apparatus for intraoral therapy. The mouthpiece apparatus may comprise at least one emitting element to emit at least one therapeutic emission. In some embodiments, the mouthpiece apparatus comprises an upper panel and a lower panel and at least one adjustable connector interconnecting the upper panel and the lower panel and adjustable to change the spacing between the upper panel and the lower panel. The mouthpiece apparatus thereby can be adjusted for a range of vestibular heights. Also provided is a related system including an adjustable mouthpiece and a related method for making an adjustable mouthpiece apparatus.

As used herein, the terms "top" and "bottom", "upper" and "lower", "upward" and "downward", "horizontal" and "vertical" and the like refer to the typical orientation of a mouthpiece apparatus for intraoral therapy when received in the mouth of a user; however, a person skilled in the art will recognize that these are relative terms that are used for ease of description only and do not limit the orientation of the mouthpiece apparatus described herein.

Figure 1A:
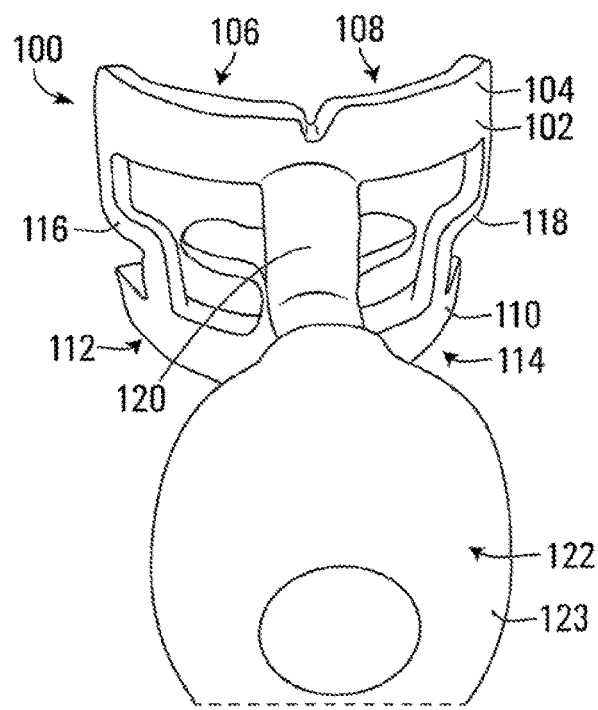
FIG. 1A is a front, perspective view of a system for intraoral therapy, including an adjustable mouthpiece apparatus, according to some embodiments.
Figure 1B:
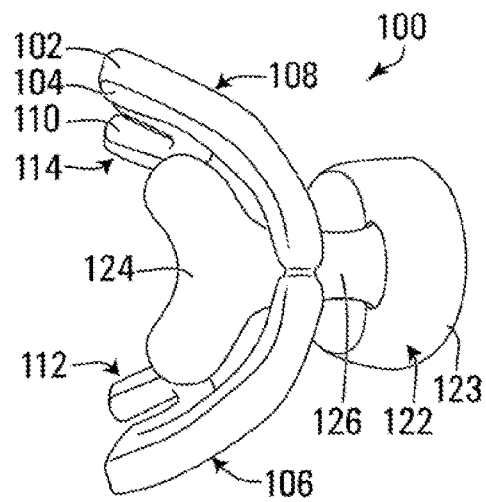
FIG. 1B is a top, perspective view of the system of FIG. 1A.

An example of a system 100, including an adjustable mouthpiece apparatus 102, for intraoral therapy will be described with reference to FIGS. 1 to 10. Referring to FIGS. 1A and 1B, in this embodiment, the system 100 comprises the adjustable mouthpiece apparatus 102 and an electronics controller 122. The mouthpiece apparatus 102 may comprise an upper panel 104 to be positioned proximate the user's maxillary teeth and a lower panel 110 to be positioned proximate the user's mandible teeth.

At least one of the upper panel 104 and the lower panel 110 may comprise at least one emitting element, as described in more detail below. The emitting element(s) may emit at least one therapeutic emission to a user's teeth, teeth roots, alveolar bone, and/or any other relevant tissue. The therapeutic emission may comprise ultrasound, light, heat, vibration, electromagnetic field, or any other suitable emission. As used herein, "therapeutic emission" refers to an emission that provides at least one beneficial effect to the user. Non-limiting examples of beneficial effects include: improved jaw bone and alveolar bone remodeling; improved healing following oral surgery or dental implanting; acceleration of orthodontic tooth movement; acceleration of tooth root remodeling; repair of tooth root resorption; acceleration of repair to jaw and alveolar bone fractures due to wisdom teeth extraction; treatment of tooth sensitivity at the root or crown level; reduction of gingiva infections; and improved healing of gingivitis and periodontitis, including healing after gingival flap surgery or alveolar bone graft surgery (two procedures used to treat periodontitis); and reduced pain or inflammation associated with oral surgery.

The mouthpiece apparatus 102 may further comprise at least one adjustable connector interconnecting the upper panel 104 and the lower panel 110 and adjustable to change the spacing between the upper panel 104 and the lower panel 110. In this embodiment, the apparatus 100 comprises a first adjustable connector 116, a second adjustable connector 118, and a third adjustable connector 120 therebetween.

In some embodiments, the mouthpiece apparatus 102 may further comprise a bite plate 124 between the upper and lower panels 104 and 110. In this embodiment, the bite plate 124 is connected to the upper and lower panels 104 and 110 via the third adjustable connector 120. In other embodiments, the bite plate 124 may be connected to at least one of the upper and lower panels 104 and 110 by any other suitable means.

In some embodiments, the mouthpiece apparatus 102 may further comprise a neck portion 126 between the upper and lower panels 104 and 110 for connecting the mouthpiece apparatus 102 to the electronics controller 122. In this embodiment, the neck portion 126 is integral with the bite plate 124 and the neck portion 126 extends from the bite plate 124 towards the electronics controller 122. In other embodiments, the neck portion 126 may be connected to at least one of the upper and lower panels 104 and 110 by any other suitable means.

The electronics controller 122 may be operatively connected to at least one of the emitting elements of the upper and lower panels 104 and 110. In some embodiments, the electronics controller 122 comprises a housing 123 to house the electronic components therein. The mouthpiece apparatus 102 may engage the electronics controller housing 123. In some embodiments, the mouthpiece apparatus 102 is permanently engaged to the housing 123. In other embodiments, the mouthpiece apparatus 102 is releasably engaged to the housing 123 such that the mouthpiece apparatus 102 and the housing 123 may be disengaged from one another to allow for replacement and/or repair of one or both of the mouthpiece apparatus 102 and the electronics controller 122. In some embodiments, the neck portion 126 of the mouthpiece apparatus 102 is at least partially received into a respective recess (not shown) in the housing 123.

Figure 2:
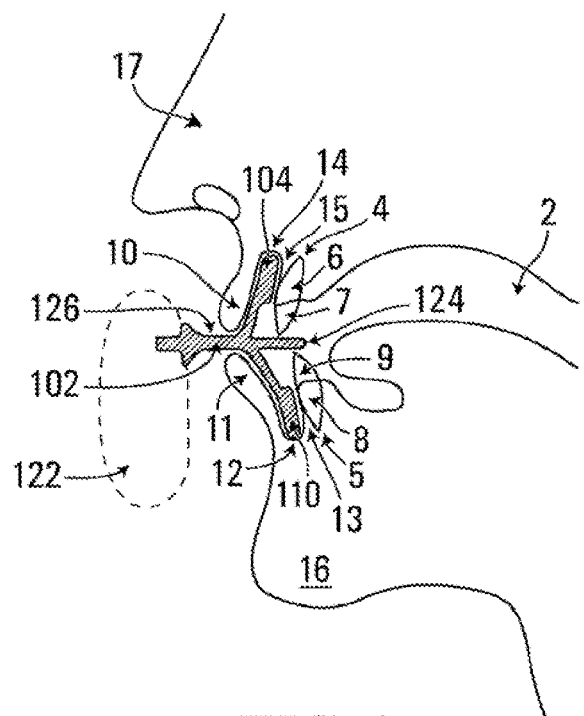
FIG. 2 is a side, cross-sectional view of the system of FIGS. 1A and 1B, shown in a mouth of a user.

FIG. 2 shows the system 100 with the mouthpiece apparatus 102 received in a user's mouth 2. The mouthpiece apparatus 102 is shown in cross-section through the middle of the mouthpiece apparatus 102

The electronics controller 122 is shown as dashed lines in FIG. 2 to illustrate where the electronics controller 122 would be located when in use by the user. The electronics controller 122 may be suitably sized such that the electronics controller 122 does not interfere with breathing through the user's nose 17. The electronics controller 122 may be positioned proximate the user's chin 16 to minimize the force generated by the weight of the electronics controller 122 on the user's mouth 2.

The upper panel 104 of the mouthpiece apparatus 102 may be received in a maxilla vestibule 14 between the user's upper lip 10 and the user's upper gums 15 on the buccal side of the maxillary teeth 4 such that the upper panel 104 is proximate the maxillary roots 6 of the maxillary teeth 4. The upper panel 104 may thereby deliver therapeutic emissions to the maxillary roots 6 of the maxillary teeth 4. The upper panel 104 may also deliver therapeutic emissions to the alveolar bone (not shown) surrounding the maxillary roots 6 and/or to any other relevant neighboring tissue.

The lower panel 110 may be received in the mandible vestibule 12 between the user's lower lip 11 and the user's lower gums 13 on the buccal side of the mandible teeth 5 such that the lower panel 110 is proximate the mandible roots 8 of the mandible teeth 5. The lower panel 110 may thereby deliver therapeutic emissions to the mandible roots 8 of the mandible teeth 5. The lower panel 110 may also deliver therapeutic emissions to the alveolar bone (not shown) surrounding the mandible roots 8 and/or to any other relevant neighboring tissue.

In some embodiments, a coupling gel (not shown) may be employed between the upper panel 104 and the upper gums 15 and the lower panel 110 and the lower gums 13 to facilitate delivery of the therapeutic emissions to the target areas. For example, in embodiments in which the therapeutic emission is ultrasound, an ultrasound coupling gel may be used.

In some embodiments, the bite plate 124 may be bit by the maxillary crowns 7 of the user's maxillary teeth 4 and the mandible crowns 9 of the user's mandible teeth 5 to help secure the mouthpiece apparatus 102 in a desired position and prevent the mouthpiece apparatus 102 from shifting within the user's mouth 2.

In some embodiments, the neck portion 126 of the mouthpiece apparatus 102 may be engaged by the user's upper and lower lips 10 and 11 to further secure the mouthpiece apparatus 102 in the desired position. In some embodiments, the neck portion 126 may be relatively thin and flat to allow the patient's upper lip 10 and lower lip 11 to touch, thereby almost completely closing the user's mouth 2 around the neck portion 126. Closing the user's mouth 2 may minimize the salivation that may be stimulated by the presence of the mouthpiece apparatus 102 as well as the coupling gel if used. In some embodiments, the user's upper and lower lips 10 and 11 may also contribute to securing the mouthpiece apparatus 102 in the desired position by pushing the upper and lower panels 104 and 110 inwards, thereby maintaining contact between the upper and lower panels 104 and 110 and the upper and lower gums 15 and 13, respectively.

Figure 3:
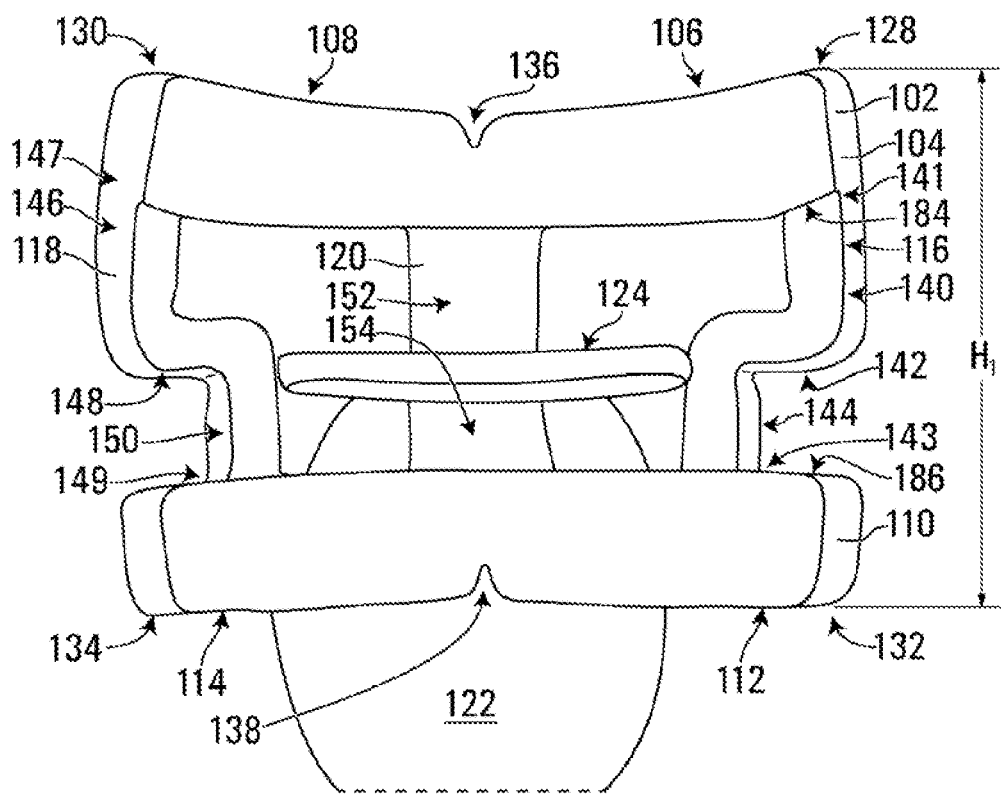
FIG. 3 is a rear, perspective view of the system of FIGS. 1A and 1B, showing the mouthpiece apparatus in an expanded position.
Figure 4:
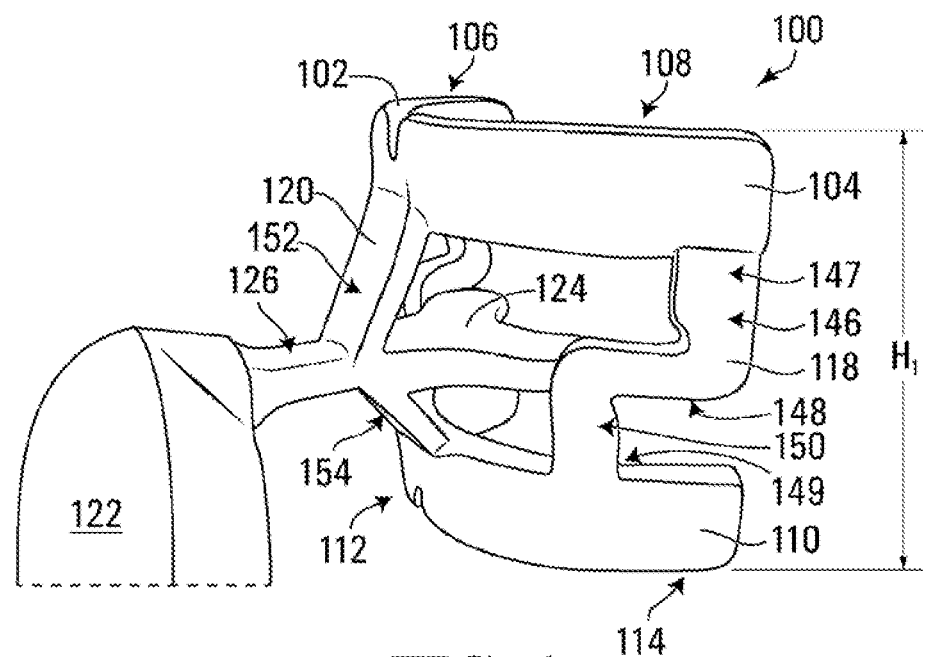
FIG. 4 is a side, perspective view of the system of FIGS. 1A and 1B, showing the mouthpiece apparatus in the expanded position.

The mouthpiece apparatus 102 may be adjustable for users with varying vestibular heights. As shown in FIGS. 3 and 4, the mouthpiece apparatus 102 may have an expanded position in which the upper panel 104 and the lower panel 110 are a maximum spacing apart. When the mouthpiece apparatus 102 is in the expanded position, a total height $H_1$ of the mouthpiece apparatus 102 approximately corresponds to a maximum total vestibular height expected for a user. In some embodiments, the total height $H_1$ of the mouthpiece apparatus 102 is approximately 55 mm when the mouthpiece is in the expanded position.

Figure 5A:
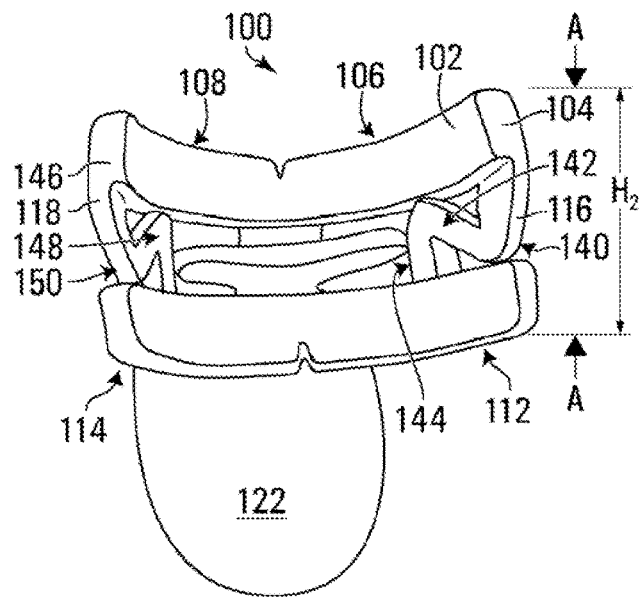
FIG. 5A is a rear, perspective view of the system of FIGS. 1A and 1B, showing the mouthpiece apparatus in a compressed position.
Figure 5B:
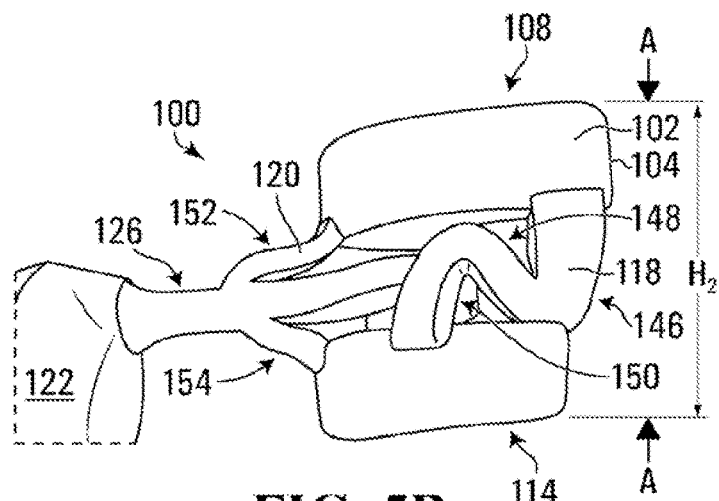
FIG. 5B is a side, perspective view of the system of FIGS. 1A and 1B, showing the mouthpiece apparatus in the compressed position.

As shown in FIGS. 5A and 5B, a force may be applied to the mouthpiece apparatus 102 to compress the upper panel 104 and the lower panel 110 towards one another, as indicated by arrows A. In some embodiments, the force may be applied when the mouthpiece apparatus 102 is received in the mouth of a user having a vestibular height shorter than the total height $H_1$ of the mouthpiece apparatus 102. As the user closes their lips 10, 11 around the neck portion 126 and bites the bite plate 124, the force may be applied to the mouthpiece apparatus 102 by the user's maxilla and mandible vestibules 14 and 12. In other embodiments, the force may be applied by the user's hand to compress the mouthpiece apparatus 102 before inserting the mouthpiece apparatus into the user's mouth 2.

Therefore, as shown in FIGS. 5A and 5B, the mouthpiece apparatus 102 may also have at least one compressed position in which the upper panel 104 and the lower panel 110 are compressed towards one another and the upper panel 104 and the lower panel 110 are less than the maximum spacing apart. When the mouthpiece apparatus 102 is in the compressed position, a total height $H_2$ of the mouthpiece apparatus 102 may be less than the maximum total vestibular height expected for a user and the total height $H_2$ may vary depending on the extent of the compression of the upper and lower panels 104 and 110 towards one another. In some embodiments, when the mouthpiece apparatus 102 is compressed, the height $H_2$ may range from approximately 25 mm up to approximately 55 mm.

In some embodiments, the adjustable connectors 116, 118, and 120 are compressible. As used herein, "compressible", when used in reference to the adjustable connectors 116, 118, and 120, refers to an ability of the adjustable connectors 116, 118, and 120 to retract and/or flex to reduce the spacing between the upper and lower panels 104 and 110. Compression of the adjustable connectors 116, 118, and 120 may thereby allow the mouthpiece apparatus 102 to be adjusted from the expanded position to the compressed position.

Therefore, in some embodiments, the mouthpiece apparatus 102 may be adjusted to allow the mouthpiece apparatus 102 to be used by a variety of users with a wide range of vestibular heights, while maintaining appropriate fit and user comfort. By adjusting the height of the mouthpiece apparatus 102, the upper and lower panels 104 and 110 may be received as deep as possible into the user's maxillary and mandibular vestibules 14 and 12 to deliver the therapeutic emissions to the maxillary and mandibular roots 6 and 8, respectively, as well as to surrounding bone and tissue as required.

The adjustable mouthpiece apparatus 102 will now be described in more detail with reference to FIGS. 3 to 7.

As shown in FIG. 3, the upper panel 104 may have a first end 128 and an opposed second end 130. The upper panel 104 in this embodiment is approximately rectangular in shape and curves from the first end 128 to the second end 130. In other embodiments, the upper panel 104 may be any other suitable shape to be received within the maxilla vestibule 14 of the user.

The upper panel 104 may comprise a first portion 106 and a second portion 108. The first portion 106 and the second portion 108 may be interconnected at a flexible connection 136 approximately midway between the first end 128 and the second end 130 of the upper panel 104. In this embodiment, the flexible connection 136 comprises an approximately V-shaped notch to provide clearance for the frenulum (not shown) of the user's upper lip 10. The first portion 106 may extend from the first end 128 to the flexible connection 136 and the second portion 108 may extend from the flexible connection 136 to the second end 130. In some embodiments, the first and second portions 106 and 108 may flex about the flexible connection 136 with respect to one another, as described in more detail below.

The lower panel 110 may have a first end 132 and an opposed second end 134. The lower panel 110 in this embodiment is approximately rectangular in shape and curves from the first end 132 to the second end 134. In other embodiments, the lower panel 110 may be any other suitable shape to be received within the mandible vestibule 12 of the user.

The lower panel 110 may comprise a first portion 112 and a second portion 114. The first portion 112 and the second portion 114 may be interconnected at a flexible connection 138 approximately midway between the first end 132 and the second end 134 of the lower panel 110. In this embodiment, the flexible connection 138 comprises an approximately V-shaped notch to provide clearance for the frenulum (not shown) of the user's lower lip 11. The first portion 112 may extend from the first end 132 to the flexible connection 138 and the second portion 114 may extend from the flexible connection 138 to the second end 134. In some embodiments, the first and second portions 112 and 114 may flex about the connection 138 with respect to one another, as described in more detail below.

In some embodiments, the upper panel 104 and the lower panel 110 are approximately parallel. In some embodiments, the first end 128 of the upper panel 104 may be approximately aligned with the first end 132 of the lower panel 110 and the second end 130 of the upper panel 104 may be approximately aligned with the second end 134 of the lower panel 110. In some embodiments, the flexible connection 136 of the upper panel 104 may also be approximately aligned with the flexible connection 138 of the lower panel 110.

In some embodiments, each of the upper and lower panel 104 and 110 may be wider than the adjustable connectors 116, 118, and 120 and may extend further lingually than the adjustable connectors 116, 118, and 120. The upper panel 104 may thereby define a first ridge 184 between the upper panel 104 and the adjustable connectors 116, 118, and 120, and the lower panel 110 may thereby define a second ridge 186 between the lower panel 110 and the adjustable connectors 116, 118, and 120, respectively (the ridges 184 and 186 are better shown in FIG. 9). The depth of the ridges 184 and 186 may be such that, if the user has orthodontic braces (not shown) such as wire braces or clear aligners, the orthodontic braces may not interfere with the adjustable connectors 116, 118, and 120.

In some embodiments, the first and second adjustable connectors 116 and 118 are laterally positioned to interconnect the upper panel 104 and the lower panel 110. The first adjustable connector 116 may interconnect the first portion 106 of the upper panel 104 and the first portion 112 of the lower panel 110. The second adjustable connector 118 may interconnect the second portion 108 of the upper panel 104 and the second portion 114 of the lower panel 110.

The third adjustable connector 120 may be centrally positioned to interconnect the upper panel 104 and the lower panel 110. The third adjustable connector 120 may be positioned approximately midway between the respective first ends 128 and 132 of the upper and lower panels 104 and 110 and the respective second ends 130 and 134 of the upper and lower panels 104 and 110.

In this embodiment, the first, second, and third adjustable connectors 116, 118, and 120 at least partially comprise a flexible resilient material. As used herein, a "flexible resilient material" refers to a material that may be flexed upon application of an external force and that returns to approximately its original shape after the force is removed. For clarity, the term "flexible resilient material" includes elastic materials that undergo elastic deformation. Non-limiting examples of suitable flexible resilient materials include elastomers and rubbers, for example: silicone elastomer and silicone rubber.

When the mouthpiece apparatus 102 is compressed, each of the first, second, and third adjustable connectors 116, 118, and 120 may exert a biasing force to push the upper and lower panels 104 and 110 apart. The biasing force may thereby push the upper and lower panels 104 and 110 into the maxilla and mandibular vestibules 14 and 12 of the user, respectively. In some embodiments, the first, second, and third adjustable connectors 116, 118, and 120 may be configured such that the biasing force exerts only mild pressure on the maxilla and mandibular vestibules 14 and 12, thereby causing little to no discomfort to the user. In some embodiments, the flexible resilient material of the first, second, and third adjustable connectors 116, 118, and 120 may be configured such that the biasing force is approximately constant for the full compression range of the first, second, and third adjustable connectors 116, 118, and 120.

In this embodiment, the first and second adjustable connectors 116 and 118 are approximately S-shaped. In some embodiments, the first and second adjustable connectors 116 and 118 are approximately symmetrical.

The first adjustable connector 116 may have an upper end 141 and a lower end 143. The upper end 141 may be connected to the first portion 106 of the upper panel 104 and the lower end 143 may be connected to the first portion 112 of the lower panel 110. In this embodiment, the upper end 141 of the first adjustable connector 116 is proximate the first end 128 of the upper panel 104 and the lower end 143 is proximate the first end 132 of the lower panel 110.

In some embodiments, the first adjustable connector 116 comprises a plurality of segments. In this embodiment, the first adjustable connector 116 comprises an upper segment 140, a middle segment 142, and a lower segment 144. The upper segment 140 may be substantially vertical and may extend downward from the upper panel 104. The lower segment 144 may be substantially vertical and may extend upward from the lower panel 110. The lower segment 144 may be horizontally offset from the upper segment 140. In some embodiments, the upper segment is approximately aligned with the first end 128 of the upper panel 104 and the lower segment 144 may be spaced inward from the first end 132 of the lower panel 110 towards the flexible connection 136. In some embodiments, the upper and lower segments 140 and 144 are approximately parallel to one another and approximately perpendicular to the upper and lower panels 104 and 110.

The middle segment 142 may be substantially horizontal and may interconnect the upper segment 140 and the lower segment 144. In some embodiments, the middle segment 142 may be approximately perpendicular to the upper and lower segments 140 and 144 and approximately parallel to the upper and lower panels 104 and 110.

Figure 7:
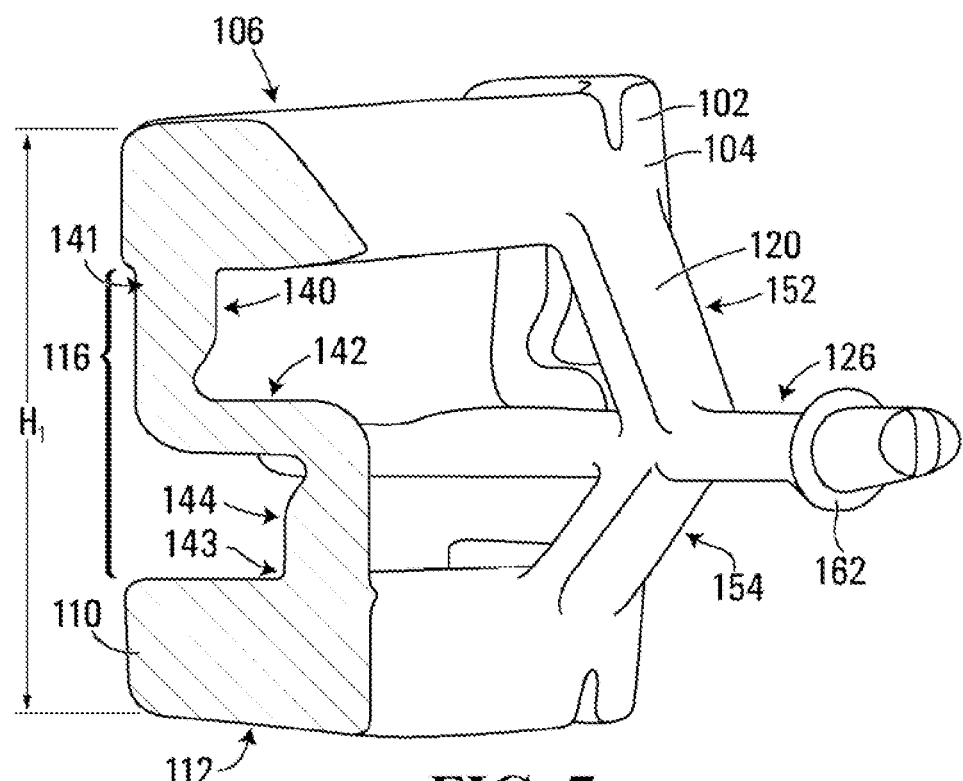
FIG. 7 is a side, perspective, partial cross-sectional view of the mouthpiece apparatus of FIGS. 1A and 1B.

In some embodiments, the upper and lower segments 140 and 144 of the first adjustable connector 116 are relatively more rigid than the middle segment 142. As shown in FIG. 7, in this embodiment, the upper and lower segments 140 and 144 comprise a thicker flexible resilient material than the middle segment 142 thereby increasing the rigidity of the upper and lower segments 140 and 144 compared to the middle segment 142. In other embodiments, the upper and lower segments 140 and 144 may each comprise a solid core therein (not shown) to increase the rigidity of the upper and lower segments 140 and 144 compared to the middle segment 142.

Referring again to FIG. 3, the second adjustable connector 118 may have an upper end 147 and a lower end 149. The upper end 147 may be connected to the second portion 108 of the upper panel 104 and the lower end 149 may be connected to the second portion 114 of the lower panel 110. In this embodiment, the upper end 147 of the second adjustable connector 118 is proximate the second end 130 of the upper panel 104 and the lower end 149 is proximate the second end 134 of the lower panel 110.

In some embodiments, the second adjustable connector 118 comprises a plurality of segments. In this embodiment, the second adjustable connector 118 comprises an upper segment 146, a middle segment 148, and a lower segment 150. The upper, middle, and lower segments 146, 148, and 150 may be similar in structure to the upper, middle, and lower segments 140, 142, and 144 of the first adjustable connector 116, as described above. In some embodiments, the upper, middle, and lower segments 146, 148, and 150 of the second adjustable connector 118 are approximately symmetrical with the upper, middle, and lower segments 140, 142, and 144 of the first adjustable connecter 116.

In some embodiments, the upper and lower segments 146 and 150 of the second adjustable connector 118 may be relatively more rigid than the middle segment 148 in a similar manner to the first adjustable connector 116, as described above.

As shown in FIGS. 5A and 5B, when a force is applied to the mouthpiece apparatus 102 to compress the upper panel 104 and the lower panel 110 towards one another, as indicated by arrows A, the middle segments 142 and 148 of the first and second adjustable connectors 116 and 118 may absorb most of the compressive force. The middle segments 142 and 148 may thereby flex to allow the upper segments 140 and 146 of the first and second adjustable connectors 116 and 118 to be displaced towards the lower panel 110 and the lower segments 144 and 150 to be displaced towards the upper panel 104. In some embodiments, the first and second adjustable connectors 116 and 118 remain approximately symmetrical when the mouthpiece apparatus 102 is in the compressed position.

Referring again to FIG. 3, in this embodiment, the third adjustable connector 120 comprises an upper portion 152 and a lower portion 154. The upper portion 152 may interconnect the upper panel 104 and the bite plate 124 and the lower portion 154 may interconnect the bite plate 124 and the lower panel 110. In other embodiments, the third adjustable connector 120 directly interconnects the upper panel 104 and the lower panel 110 without the bite plate 124 therebetween.

As shown in FIG. 4, the upper portion 152 of the third adjustable connector 120 in this embodiment extends from the upper panel 104 and connects to the bite plate 124 at an angle of less than 90°. The lower portion 154 of the third adjustable connector 120 in this embodiment extends from the lower panel 110 and connects to the bite plate 124 at an angle of less than 90°. In some embodiments, the angle between the upper portion 152 and the bite plate 124 and the angle between the bite plate 124 and the lower portion 154 are close to or approximately equal, thereby allowing the upper portion 152 and the lower portion 154 to be compressed in a similar manner.

In this embodiment, each of the upper and lower portions 152 and 154 comprises a relatively thin layer of flexible resilient material. In some embodiments, the flexible resilient material of the third adjustable connector 120 is the same flexible resilient material as the first and second adjustable connectors 116 and 118. In other embodiments, the flexible resilient material of the third adjustable connector 120 may be a different flexible resilient material than the first and second adjustable connectors 116 and 118.

As shown in FIG. 5B, when a force is applied to the mouthpiece 102 as indicated by arrows A, both the upper and lower portions 152 and 154 of the third adjustable connector 120 may flex to allow the upper and lower panels 104 and 110 to move closer together.

Therefore, in some embodiments, the first, second, and third adjustable connectors 116, 118, and 120 allow compression of the mouthpiece apparatus 102 in an approximately symmetrical fashion such that the upper and lower panels 104 and 110 remain approximately parallel. The upper and lower panels 104 and 110 may thereby be suitably positioned to deliver therapeutic emissions across a wide range of vestibular heights.

In other embodiments, the mouthpiece apparatus 102 may comprise only the third adjustable connector 120 and not the first and second adjustable connectors 116 and 118. In other embodiments, the mouthpiece apparatus 102 may comprise one or both of the first and second adjustable connectors 116 and 118 and not the third adjustable connector 120. In other embodiments, the mouthpiece apparatus 102 may comprise any other suitable adjustable connector or combination of adjustable connectors.

Figure 6A:
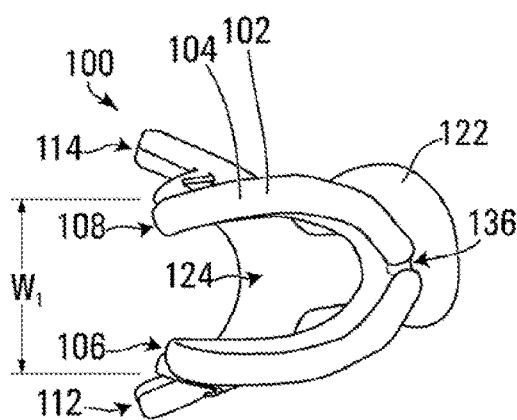
FIG. 6A is a top, perspective view of the system of FIGS. 1A and 1B, showing an upper panel of the mouthpiece apparatus in a narrow configuration.
Figure 6B:
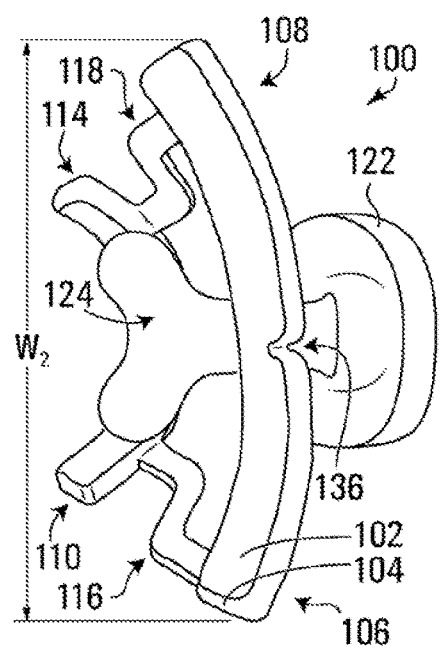
FIG. 6B is a top, perspective view of the system of FIGS. 1A and 1B, showing the upper panel of the mouthpiece apparatus in a wide configuration.

In some embodiments, at least one of the upper and lower panels 104 and 110 of the mouthpiece apparatus 102 may also be adjustable for users with a range of dental arch widths. FIG. 6A shows the mouthpiece apparatus 102 with the upper panel 104 in a relatively narrow configuration, having a total width W. FIG. 6B shows the mouthpiece apparatus 102 with the upper panel 104 in a relatively wide configuration, having a total width W2, the total width W2 being greater than the total width W. In both narrower and wider configurations, the bite plate 124 may still be accessible to the user to be bitten.

To adjust the upper panel 104 into a narrower configuration, the first and second portions 106 and 108 of the upper panel 104 may be flexed towards one another. To adjust the upper panel 104 into a wider configuration, the first and second portions 106 and 108 may be flexed away from one another. In some embodiments, the first portion 106 and the second portion 108 of the upper panel 104 may be flexed with respect to one another about the flexible connection 136. The first and second portions 112 and 114 of the lower panel 110 may be similarly flexed about the flexible connection 138 (not visible in FIGS. 6A and 6B). In some embodiments, the flexible connections 136 and 138 may each comprise a flexible resilient material to allow the upper and lower panels 104 and 110 to flex about the flexible connections 136 and 138. In some embodiments, the flexible resilient material of the flexible connections 136 and 138 is the same or similar flexible resilient material as the adjustable connectors 116, 118, and 120.

In some embodiments, the flexible nature of the adjustable connectors 116, 118, and 120 also allows the upper and lower panels 104 and 110 to be flexed about the flexible connections 136 and 138 without being restricted by the presence of the adjustable connectors 116, 118, and 120.

Figure 9:
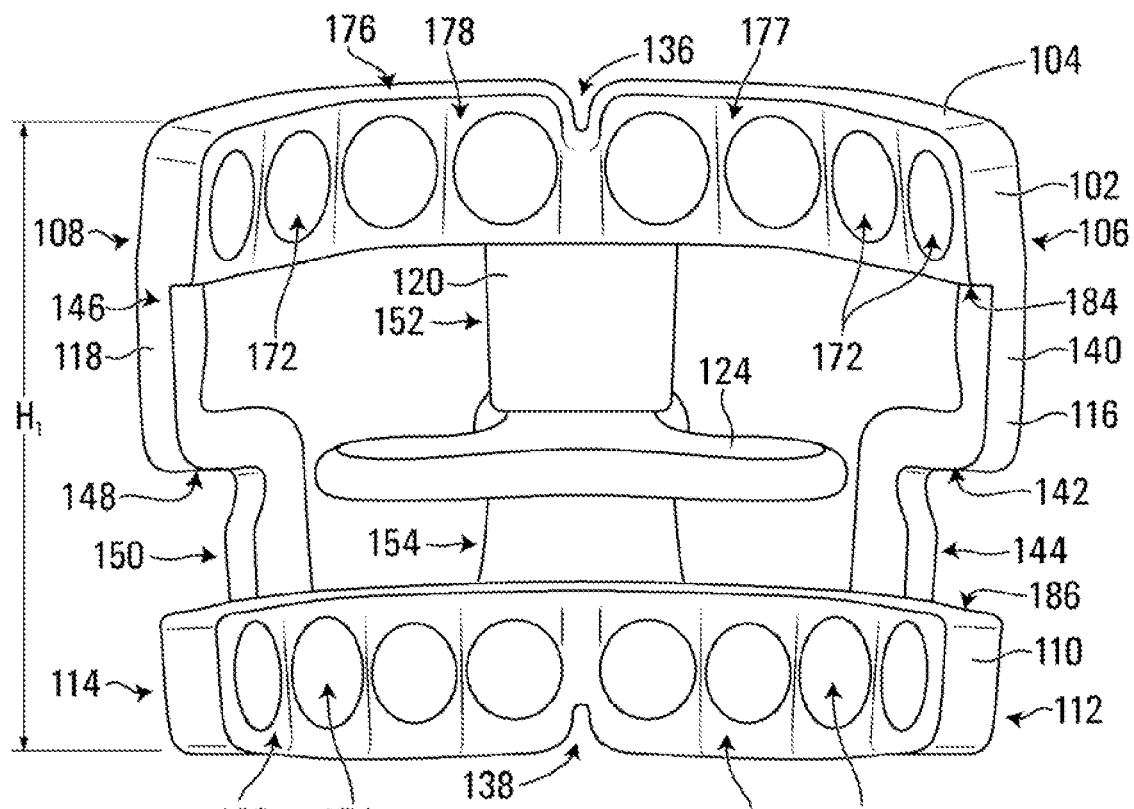
FIG. 9 is a rear, perspective, partial cross-sectional view of the mouthpiece apparatus of FIGS. 1A and 1B.
Figure 10:
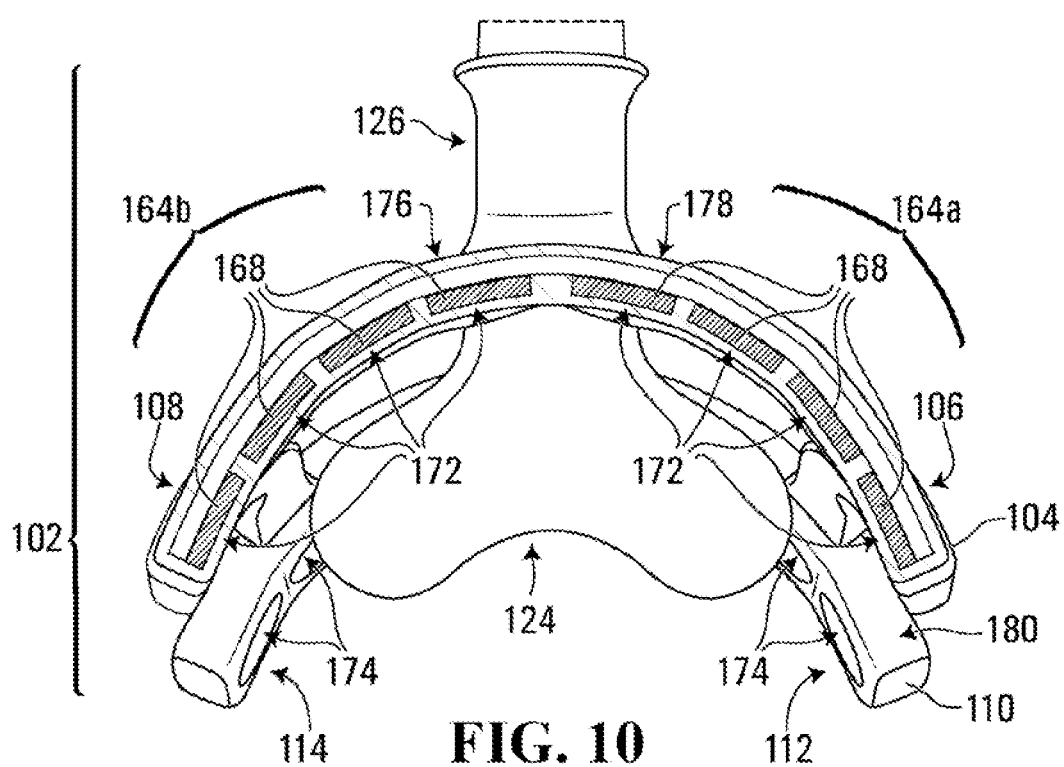
FIG. 10 is a top, perspective, partial cross-sectional view of the mouthpiece apparatus of FIGS. 1A and 1B.

The emitting elements of the mouthpiece apparatus 102 will now be described in more detail with reference to FIGS. 8 to 10.

Figure 8:
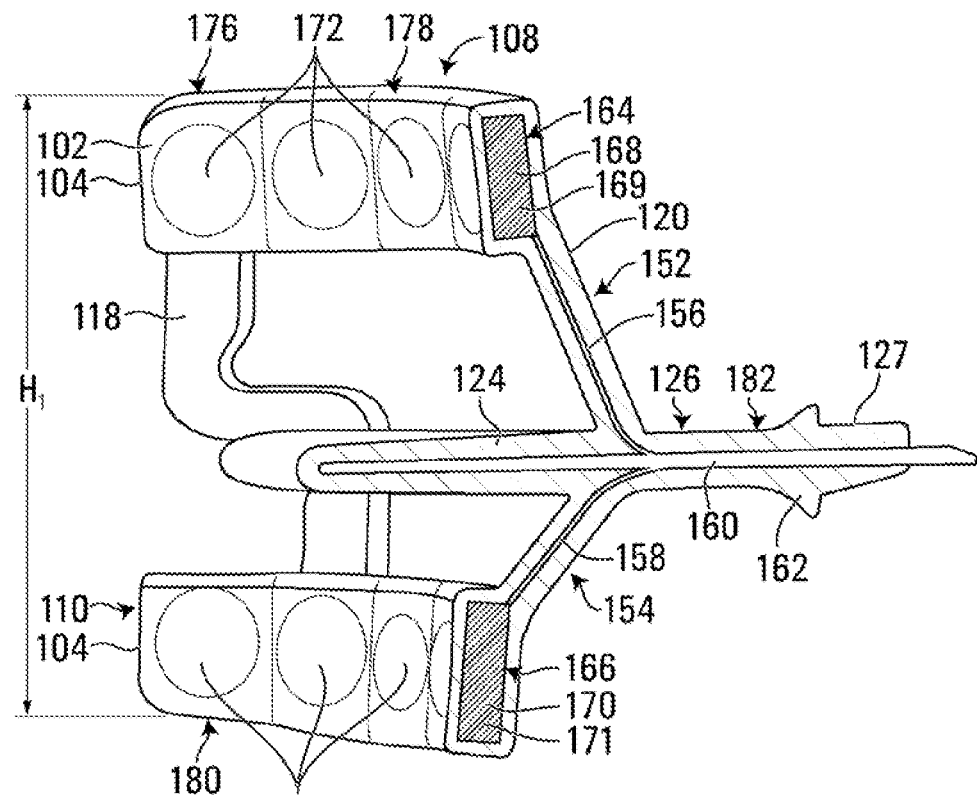
FIG. 8 is a side, perspective, partial cross-sectional view of the mouthpiece apparatus of FIGS. 1A and 1B.

Referring to FIG. 8, the upper panel 104 of the mouthpiece apparatus 102 may comprise at least one first emitting element 168 and the lower panel 110 may comprise at least one second emitting element 170. In this embodiment, the first and second emitting elements 168 and 170 comprise a first and second ultrasound transducer 169 and 171, respectively.

In some embodiments, the ultrasound transducers 169 and 171 each comprise a piezoelectric ultrasound transducer. In some embodiments, the piezoelectric transducer may be a bulk (thickness mode) piezoelectric transducer driven at or close to resonance. The piezoelectric transducer may be circular, square, rectangular, or any other suitable shape. In some embodiments, the length to width ratio of the piezoelectric transducer may be close to one. An example of a suitable piezoelectric transducer is one that is approximately circular, made of PZT (lead zirconate titanate), has a thickness of approximately 1.4 mm (which represents half of the wavelength of the resonant frequency of 1.5 MHz in the PZT material), and has a diameter of approximately 28 mm or less (which represents ten wavelengths of the resonant frequency of 1.5 MHz in the PZT material). In some embodiments, a backing to the transducer may comprise air or a low acoustic impedance material such as foam. Additional details regarding suitable ultrasound transducers may be found, for example, in U.S. Pat. No. 9,232,986, incorporated herein by reference. In other embodiments, the first and second emitting elements 168 and 170 may comprise any other suitable ultrasound emitting elements and embodiments are not limited to the ultrasound transducers described herein.

In other embodiments, the first and second emitting elements 168 and 170 may each comprise one of a light emitting element, a heat emitting element, a vibration emitting element, an electromagnetic emitting element, or any other type of emitting element that may be used to provide therapeutic emissions to the user. In some embodiments, the light and/or heat emitting element may comprise a light emitting diode (LED). In some embodiments, the vibration emitting element may comprise a small, vibration motor. In some embodiments, the electromagnetic field emitting element may comprise a small antenna. In some embodiments, the first and second emitting elements 168 and 170 are the same type of emitting element. In other embodiments, the first and second elements 168 and 170 may comprise different types of emitting elements.

In this embodiment, the upper panel 104 comprises an upper array 164 of emitting elements 168 and the lower panel 110 comprises a lower array 166 of emitting elements 170. In this embodiment, the upper and lower arrays 164 and 166 are flexible arrays. As shown in FIG. 10, the first portion 106 of the upper panel 104 comprises a first array portion 164a and the second portion 108 of the upper panel 104 comprises a second array portion 164b. The first and second array portions 164a and 164b may each comprise four first emitting elements 168 such that the upper array 164 comprises eight emitting elements 168 total. Similarly, the lower array 166 of the lower panel 110 may comprise a first and second array portion (not shown) and each of the first and second array portions comprising four emitting elements 170. In other embodiments, the upper panel 104 and the lower panel 110 may each comprise any suitable number of emitting elements 168 and 170, respectively. Embodiments are not limited by the number or arrangement of emitting elements as described herein.

In this embodiment, all of the first emitting elements 168 of the upper array 164 comprise ultrasound transducers 169. In other embodiments, the first emitting elements 168 of the upper array 164 may comprise two or more different types of emitting elements. Similarly, all of the emitting elements 170 of the lower array 166 in this embodiment comprise ultrasound transducers 171. In other embodiments, the emitting elements 170 of the lower array 166 may comprise two or more different types of emitting elements.

In some embodiments, the mouthpiece apparatus 102 comprises at least one flexible circuit board (FCB) operatively connected to the upper and lower arrays 164 and 166. The FCB may also be operatively connected to the electronics controller 122 to allow the upper and lower arrays 164 and 166 to be controlled by the electronics controller 122. As shown in FIG. 8, in this embodiment, the upper array 164 is operatively connected to a first FCB 156 and the lower array 166 is operatively connected to a second FCB 158.

At least a portion of the first and second FCBs 156 and 158 may be disposed within the third adjustable connector 120. In this embodiment, the first FCB 156 extends from the upper array 164, through the first portion 152 of the third adjustable connector 120, to the bite plate 124. Within the bite plate 124, the first FCB 156 may be coupled to a bite plate core 160. The bite plate core 160 may comprise a relatively hard material, for example, a metal, hard plastic, or any other suitable material. The bite plate core 160 may extend out of the neck portion 126 towards the electronics controller 122. The first FCB may thereby extend out of the neck portion 126, with the bite plate core 160, to connect to the electronics assembly 122. The first FCB 156 may be coupled to the bite plate 124 using a suitable adhesive or any other suitable coupling means.

The second FCB 158 may extend from the lower array 166, through the second portion 154 of the third adjustable connector 120, to the bite plate 124. Within the bite plate 124, the second FCB 158 may be coupled to the bite plate core 160 and the second FCB 158 may extend out of the neck portion 126 with the bite plate core 160 to connect to the electronics assembly 122. By operatively connecting the upper and lower arrays 164 and 166 to the electronics controller 122 by flexible circuit boards 156 and 158, the first and second portions 152 and 154 of the third adjustable connector 120 may still be capable of flexing without damaging the FCBs 156 and 158.

In some embodiments, at least a portion of the mouthpiece apparatus 102 is encapsulated in a flexible casing 176. In some embodiments, the flexible casing 176 comprises a flexible resilient material. In some embodiments, the flexible resilient material is the same or similar to the flexible resilient material of the adjustable connectors 116, 118, and 120. For example, the flexible resilient material may be an elastomer or rubber material, such as silicone elastomer or silicone rubber.

As shown in FIG. 8, in some embodiments, at least one emitting element 168, 170 is encapsulated in the flexible casing 176. In this embodiment, the upper array 164 of emitting elements 168 is encapsulated in a first flexible casing portion 178 and the lower array 166 of emitting elements 170 is encapsulated in a second flexible casing portion 180. In some embodiments, the thickness of the flexible casing portions 178 and 180 proximate the emitting elements 168 and 170 is approximately the same or similar to the thickness of the emitting elements 168 and 170 themselves; for example, approximately the thickness of ultrasound transducers 169 and 171. In other embodiments, the thickness of the flexible casing portions 178 and 180 may be any other suitable thickness to allow the therapeutic emissions from the emitting elements 168 and 170 to pass through the flexible casing portions 178 and 180 to the target areas of the user.

In some embodiments, the first flexible casing portion 178 may at least partially surround each of the first emitting elements 168 in the upper array 164 such that portions of flexible resilient material are disposed between each of the emitting elements 168. Therefore, in embodiments in which the upper array 164 is a flexible array, the combination of the flexible resilient material between the emitting elements 168 and the flexible nature of the upper array 164 may allow the upper panel 104 to flex between each of the first emitting elements 168. Similarly, in some embodiments, the second flexible casing portion 178 may at least partially surround each of the second emitting elements of the lower array 168 such that portions of flexible resilient material are disposed between each of the emitting elements 170, thereby allowing the lower panel 110 to flex between each of the second emitting elements 170.

In some embodiments, at least one of the flexible casing portions 178, 180 define at least one depression proximate at least one emitting element. As shown in FIGS. 9 and 10, an inner wall 177 of the first flexible casing portion 178 defines at least one first depression 172 proximate at least one first emitting element 168 of the upper array 164 (note that the first emitting elements 168 and the upper array 164 are not shown in FIG. 9). An inner wall 179 of the second flexible casing 180 may define at least one second depression 174 proximate at least one second emitting element 170 of the lower array 166 (note that the second emitting elements 170 and the lower array 166 are not shown in FIGS. 9 and 10). In this embodiment, the inner wall 177 of the first casing portion 178 defines eight first depressions 172, each first depression 172 proximate a respective first emitting element 168 of the upper array 164. The inner wall 179 of the second flexible casing 180 may also define eight second depressions 174, each second depression 174 proximate a respective second emitting element 170 of the lower array 166. When the mouthpiece apparatus 102 is received in a user's mouth, the depressions 172 and 174 in the respective inner walls 177 and 179 of first and second casing portions 178 and 180 may face the user's maxillary roots 6 and mandible roots 8, respectively.

In some embodiments, each of the first and second depressions 172 and 174 are relatively shallow, concave depressions. In this embodiment, each depression 172 and 174 has a depth of approximately 200 µm. In other embodiments, each depression 172 and 174 may have any other suitable depth. In this embodiment, each of the first and second depressions 172 and 174 are approximately circular. In other embodiments, each of the first and second depressions 172 and 174 may be approximately oval, elliptical, or any other suitable shape. In some embodiments, each of the first and second depressions 172 and 174 are approximately centered on a respective first and second emitting element 168 and 170.

In this embodiment, the depressions 172 and 174 function to increase the effective radiating area (ERA) and reduce the beam non-uniformity ratio (BNR) of the ultrasound transducers 169 and 171. In embodiments in which the emitting elements 168 and 170 are light emitting elements, the depressions 172 and 174 may function to collimate the light emitted by the light emitting elements. In other embodiments, the depressions may provide any other useful effect on the therapeutic emissions emitted by the emitting elements 168 and 170, including but not limited to increasing the amount or intensity of the therapeutic emissions delivered to the target tissues of the user. Therefore, in some embodiments, the depressions 172 and 174 may improve the delivery of the therapeutic emissions to the user's maxillary roots 6 and mandible roots 8, and any other target bone and/or tissue.

In some embodiments, additional components of the mouthpiece apparatus 102 may also be encapsulated in a flexible casing. In this embodiment, as shown in FIG. 8, the bite plate 124 and the neck portion 126 are encapsulated in third flexible casing portion 182. The third flexible casing portion 182 may comprise a flexible resilient material as described above for the first and second flexible casings 178 and 180. In some embodiments, the third flexible casing portion 182 comprises an annular ridge 162 to form a seal around the electronic housing assembly 123 (not shown in FIG. 8) when an end section 127 of the neck portion is received in a respective recess (not shown) of the housing 123.

In some embodiments, the first, second, and third flexible casing portions 178, 180, and 182 as well as the first, second, and third adjustable connectors 116, 118, and 120 are all made of the same flexible resilient material. In some embodiments, the flexible casing portions 178, 180, and 182 and adjustable connectors 116, 118, and 120 are integrally formed. In other embodiments, one or more of the flexible casing portions 178, 180, and 182 and adjustable connectors 116, 118, and 120 may be made of different materials. In some embodiments, one or more of the flexible casing portions 178, 180, and 182 and adjustable connectors 116, 118, and 120 may be coupled to one another by any suitable means.

Figure 11:
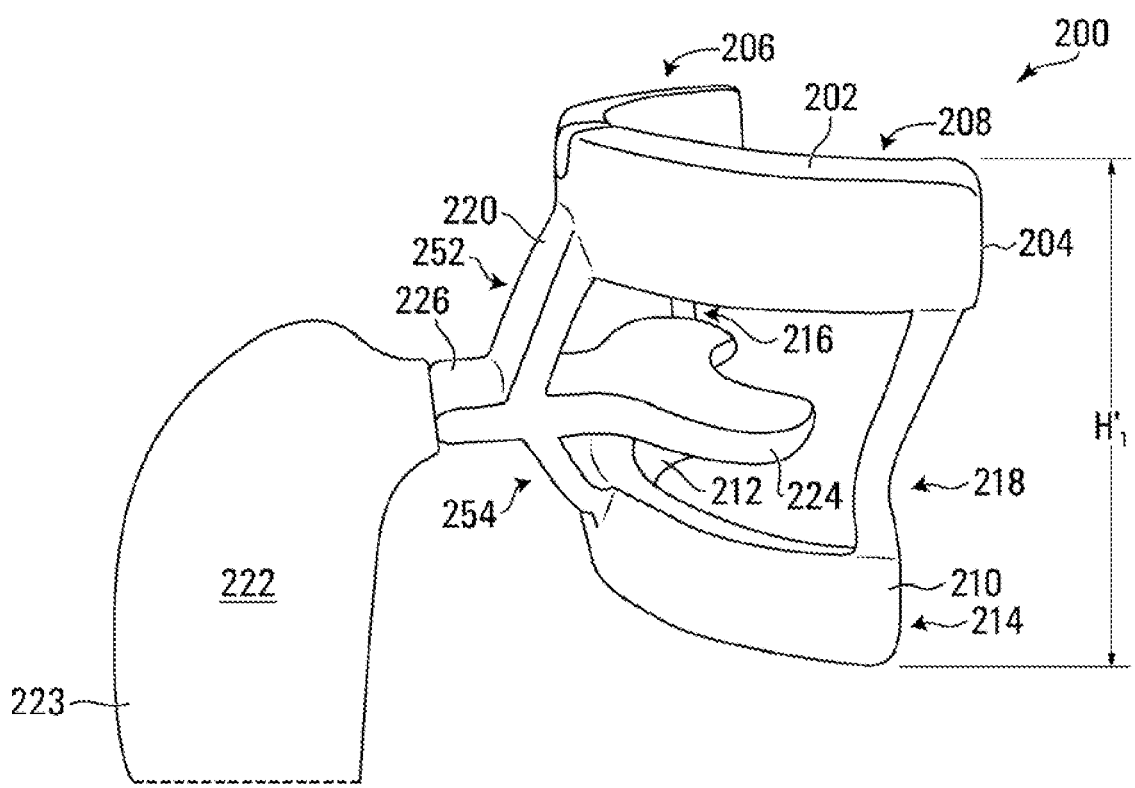
FIG. 11 is a side, perspective view of another system for intraoral therapy, including an adjustable mouthpiece apparatus, according to some embodiments, showing the mouthpiece apparatus in an expanded position.

A second example of a system 200, including an adjustable mouthpiece apparatus 202, for intraoral therapy will now be described with reference to FIGS. 11 and 12. As shown in FIG. 11, the system 200 in this embodiment comprises the adjustable mouthpiece apparatus 202 and an electronics controller 222.

The mouthpiece apparatus 202 may comprise an upper panel 204 and a lower panel 210. At least one of the upper panel 204 and the lower panel 210 may comprise at least one emitting element (not shown). The emitting element may be similar to the emitting elements 168 and 170 of the mouthpiece apparatus 102 as described above. In this embodiment, the upper panel 204 comprises a first portion 206 and a second portion 208. The lower panel 210 may comprise a first portion 212 and a second portion 214.

The mouthpiece apparatus 202 may further comprise a bite plate 224 and a neck portion 226. In this embodiment, the neck portion 226 has an end section 227 to be received in a respective recess (not shown) in a housing 223 of the electronics controller 222. The electronics controller 222 may be operatively connected to the emitting element(s) of the mouthpiece apparatus 202.

The mouthpiece apparatus 202 in this embodiment comprises a first adjustable connector 216, a second adjustable connector 218, and a third adjustable connector 220 therebetween. The first, second, and third adjustable connectors 216, 218, and 220 may be compressible and compression of the first, second, and third adjustable connectors 216, 218, and 220 may allow the upper and lower panels 204 and 210 to move towards one another and thereby reduce the spacing between the upper and lower panels 204 and 210.

The first adjustable connector 216 may interconnect the first portion 206 of the upper panel 204 and the first portion 212 of the lower panel 210. The second adjustable connector 218 may interconnect the second portion 208 of the upper panel 204 and the second portion 214 of the lower panel 210. In some embodiments, the first and second adjustable connectors 216 and 218 are approximately symmetrical.

The third adjustable connector 220 may be centrally positioned approximately midway between the first and second adjustable connectors 216 and 218. The third adjustable connector may comprise an upper portion 252 and a lower portion 254. The upper portion 252 may connect the upper panel 204 to the bite plate 224 and the lower portion 254 may connect the bite plate 224 and the lower panel 210.

In this embodiment, the first, second, and third adjustable connectors 216, 218, and 220 at least partially comprise a plastically deformable material. As used herein, "plastically deformable" refers to a material that may be deformed into a different shape or position upon application of external force and that retains its deformed shape or position after the force is removed. In this embodiment, the plastically deformable material comprises one or more metal wires. In some embodiments, the metal wires are formed into a wire mesh. In other embodiments, the plastically deformable material may comprise any other suitable material and embodiments are not limited to the materials described herein.

In some embodiments, the one or more metal wires are incorporated in a flexible resilient material. As used herein, "incorporated" may refer to encapsulating or embedding the metal wires in the flexible resilient material or otherwise combining the metal wires and flexible resilient material by any suitable means. The flexible resilient material may be, for example, an elastomer or rubber such as silicone elastomer or silicone rubber. In other embodiments, the flexible resilient material may be any other suitable material. In some embodiments, the same or a similar flexible resilient material may be used to encapsulate at least a portion of the mouthpiece apparatus 202 in a flexible casing in a similar manner as described above with respect to mouthpiece apparatus 102.

The mouthpiece apparatus 202 may be adjustable via the first, second, and third adjustable connectors 216, 218, and 220. As shown in FIG. 11, the mouthpiece apparatus 202 may have an expanded position in which the upper and lower panels 204 and 210 are a maximum spacing apart. When the mouthpiece apparatus 202 is in the expanded position, a total height $H'_1$ of the mouthpiece apparatus 202 approximately corresponds to a maximum total vestibule height expected for a user.

Figure 12:
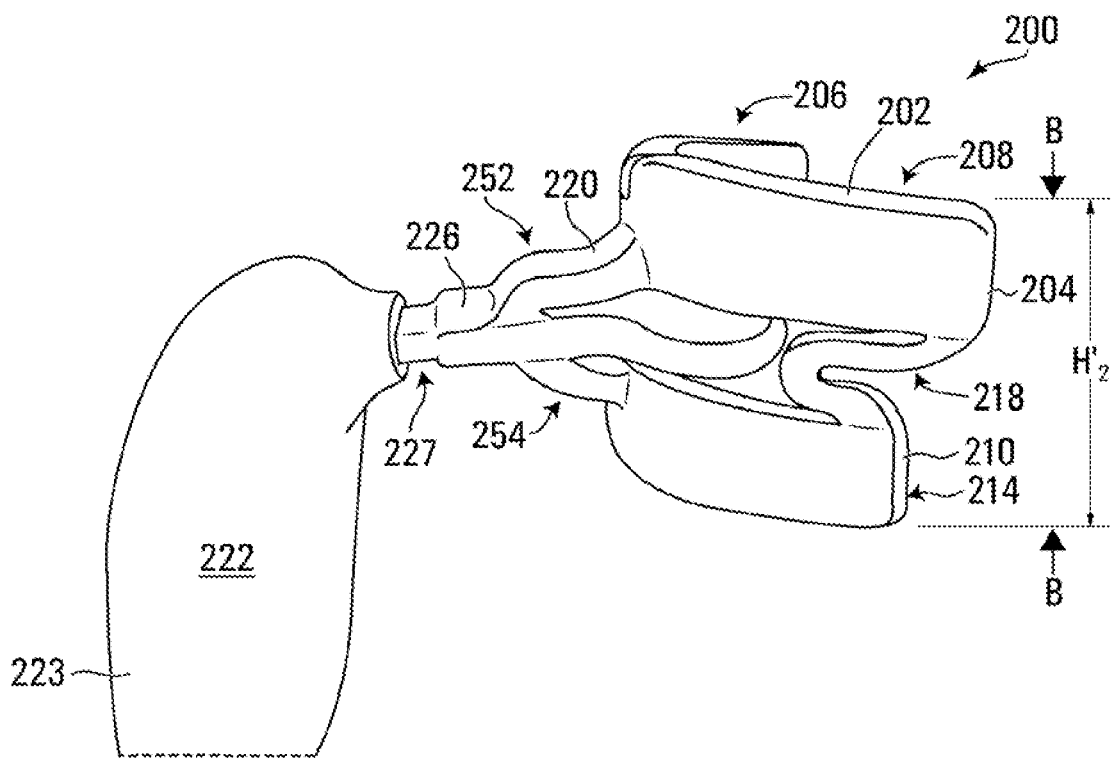
FIG. 12 is a side, perspective view of the system of FIG. 11, showing the mouthpiece apparatus in a compressed position.

As shown in FIG. 12, the mouthpiece apparatus 202 may also have at least one compressed position in which the upper panel 204 and the lower panel 210 are compressed towards one another and the upper and lower panels 204 and 210 are less than the maximum spacing apart. When the mouthpiece apparatus 202 is in the compressed position, a total height $H'_2$ of the mouthpiece may vary depending on the extent of the compression of the upper and lower panels 204 and 210 towards one another.

When a force is applied to the mouthpiece apparatus 202 to compress the upper and lower panels 204 and 210 towards one another, as indicated by arrows B, each of the first, second, and third adjustable connectors 216, 218, and 220 may be deformed to allow the upper and lower panels 204 and 210 to move towards one another. The first, second, and third adjustable connectors 216, 218, and 220 may remain in their deformed state after the force is removed. In some embodiments, the first, second, and third adjustable connectors 216, 218, and 220 may be manually re-adjusted to their original state if needed.

Figure 13:
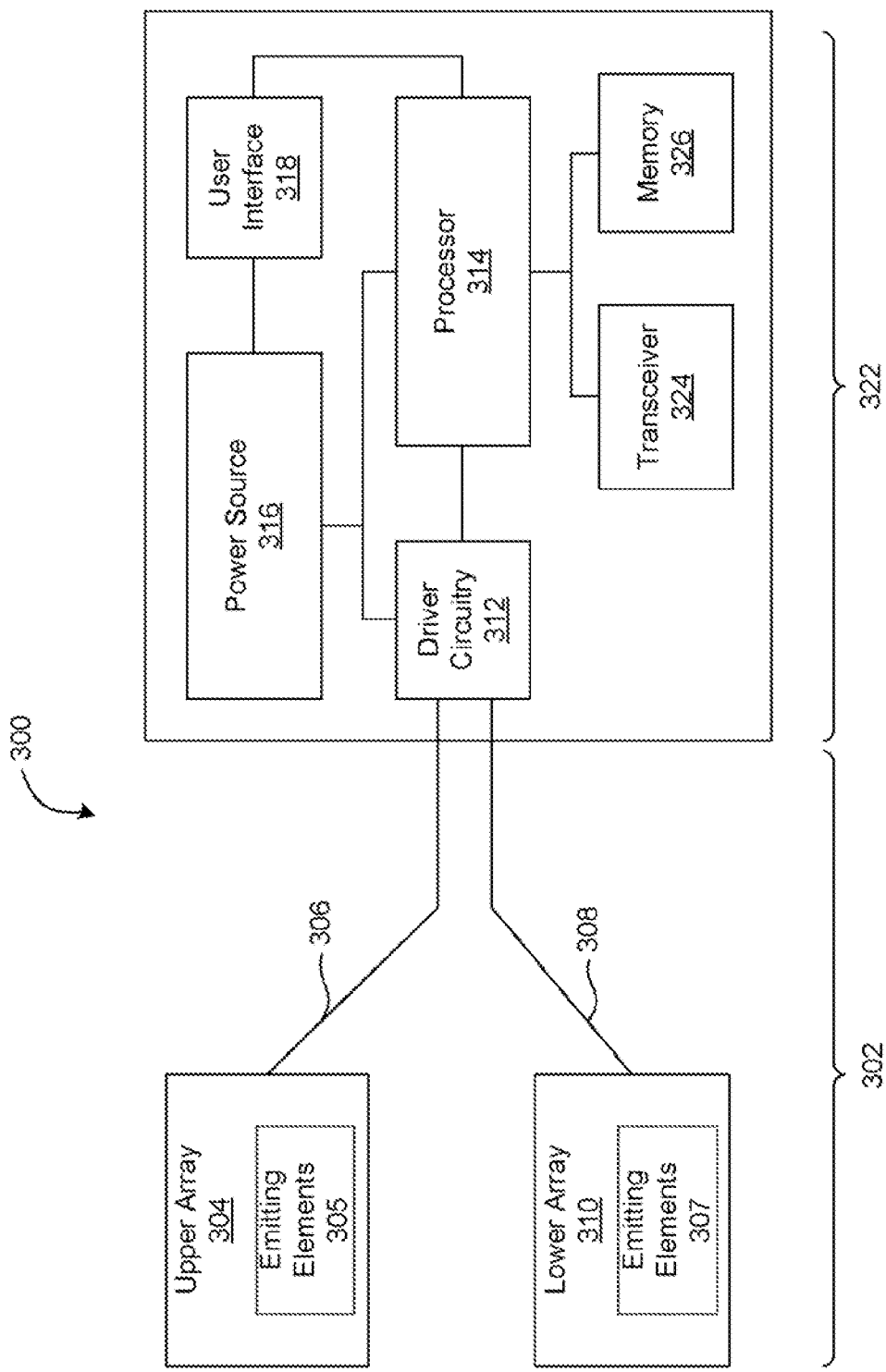
FIG. 13 is a functional block diagram of another system for intraoral therapy, including an adjustable mouthpiece apparatus, according to some embodiments.

FIG. 13 is a functional block diagram of a system 300 for intraoral therapy according to some embodiments. The system 300 in this embodiment comprises an adjustable mouthpiece apparatus 302 and an electronics controller 322. The mouthpiece apparatus 302 and the electronics controller 322 may be similar in structure to the mouthpiece apparatus 102 or 202 and the electronics controller 122 or 222, as described above with reference to FIGS. 1 to 12.

The mouthpiece 302 in this embodiment comprises an upper array 304 of emitting elements 305 and a lower array 310 of emitting elements 307. In some embodiments, the emitting elements 305 and 307 are ultrasound transducers as described above. In other embodiments, the emitting elements 305 and 307 are any other suitable type of emitting element.

The electronics controller 322 in this embodiment comprises a driver circuitry 312, a processor 314, a power source 316, a user interface 318, a transceiver 324, and a memory 326.

The upper array 304 may be operatively connected to the driver circuitry 312 by a first flexible circuit board 306 and the lower array 310 may be operatively connected to the driver circuitry 312 by a second flexible circuit board 308. The driver circuitry 312 may drive the emitting elements 305, 307 of the upper and lower arrays 304 and 310. In some embodiments, the driver circuitry 312 comprises a plurality of drivers such that the upper and lower arrays 304 and 310 may be driven independently and, in some embodiments, such that each emitting element 305, 307 may be driven independently.

The driver circuitry 312 may be operatively connected to the power source 316 and the processor 314. In some embodiments, the power source 316 comprises a battery. In some embodiments, the power source 316 further comprises an inductive charging coil (not shown) and battery charging circuitry (not shown) to allow the battery to be inductively charged. In other embodiments, the power source 316 may comprise any other suitable power source. In some embodiments, the electronics controller 322 may further comprise at least one voltage regulator (not shown) to regulate the voltage from the power source 316.

The processor 314 may process user input from the user interface 318 and activate the driver circuitry 312 in response to user input. In some embodiments, the user interface 318 comprises a control such as a button. In some embodiments, the user interface 318 further comprises at least one light source (not shown), such as one or more LEDs, to indicate one or more statuses of the system 300. For example, the LEDs may emit one color of light when the system 300 is active and another color of light when if the system 300 encounters an error.

The memory 326 is operatively connected to the processor 314. The memory 326 may store processor-executable instructions to be executed by the processor 314. For example, the memory 326 may store instructions for specific treatment regimens to be implemented by the system 300, including pulse duration, intensity, etc. settings for the emitting elements 305 and 307.

The transceiver 324 is also operatively connected the processor 314. The transceiver 324 may be configured to send and receive communications over a communication network such as the Internet. In some embodiments, the transceiver 324 comprises a Bluetooth transceiver. In some embodiments, the transceiver 324 comprises both a transmitter and receiver sharing common circuitry. In other embodiments, the transceiver 324 comprises a separate transmitter and receiver.

In some embodiments, the electronics controller 322 may thereby transmit information, via the communication network, regarding the use and operation of the system 300 to the user and/or to the user's medical provider. For example, the electronics controller 322 may transmit information regarding how often the user has activated the arrays 304, 310 of the mouthpiece apparatus 302 by pressing the button. The electronics controller 322 may also receive information, via the communication network, from the user or the user's medical provider. For example, the user's medical provider may transmit instructions for a new treatment regimen.

In some embodiments, the system 300 comprises any other suitable components, for example, an RF (radio frequency) signal generator, EMC (electromagnetic compatibility) filters, and/or any other suitable component.

A method of making an adjustable mouthpiece apparatus for intraoral therapy is also provided. The method may be used to make embodiments of the mouthpiece apparatus 102, 202 described herein.

Figure 14:
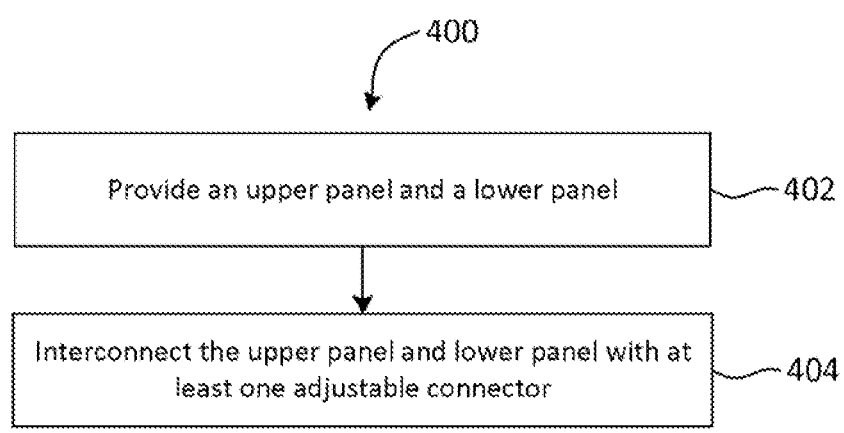
FIG. 14 a flowchart of an example method for making a mouthpiece apparatus for intraoral therapy, according to some embodiments.

FIG. 14 is a flowchart of an example method 400 for making a mouthpiece apparatus according to some embodiments. At block 402, an upper panel and a lower panel are provided. In some embodiments, at least one of the upper panel and the lower panel may comprise at least one emitting element. The upper and lower panels may be similar in structure to the upper panel 104, 204 and the lower panel 110, 210 as described above. As used herein, "providing" the upper and lower panels refers to making, manufacturing, receiving, or otherwise obtaining the upper and lower panels.

In some embodiments, providing the upper and lower panels comprises providing an upper array of emitting elements and a lower array of emitting elements. The upper array and lower array may be similar in structure to the upper array 164 and the lower array 166 as described above. In some embodiments, the emitting elements comprise at least one of an ultrasound emitter, a light emitter, a heat emitter, a vibration emitter, and an electromagnetic field emitter.

At block 404, the upper panel and lower panel may be interconnected with at least one adjustable connector. The adjustable connector(s) may be similar in structure to one of the adjustable connectors 116, 118, and 120 of the mouthpiece apparatus 102 or the adjustable connectors 216, 218, 220 of the mouthpiece apparatus 202. In some embodiments, the adjustable connector(s) at least partially comprise a flexible resilient material. In some embodiments, the adjustable connector(s) at least partially comprise a plastically deformable material.

In some embodiments, the method 400 further comprises encapsulating each of the upper and lower panels in a respective flexible casing. In some embodiments, interconnecting the upper and lower panels with the at least one adjustable connector comprises integrally forming the flexible casings and the adjustable connector(s). In some embodiments, the flexible casings and adjustable connector(s) are formed of a flexible resilient material.

In other embodiments, interconnecting the upper panels and the lower panels may comprise coupling the upper panel to a first end of an adjustable connector and coupling the lower panel to a second end of the adjustable connector using any suitable coupling means.

Figure 15:
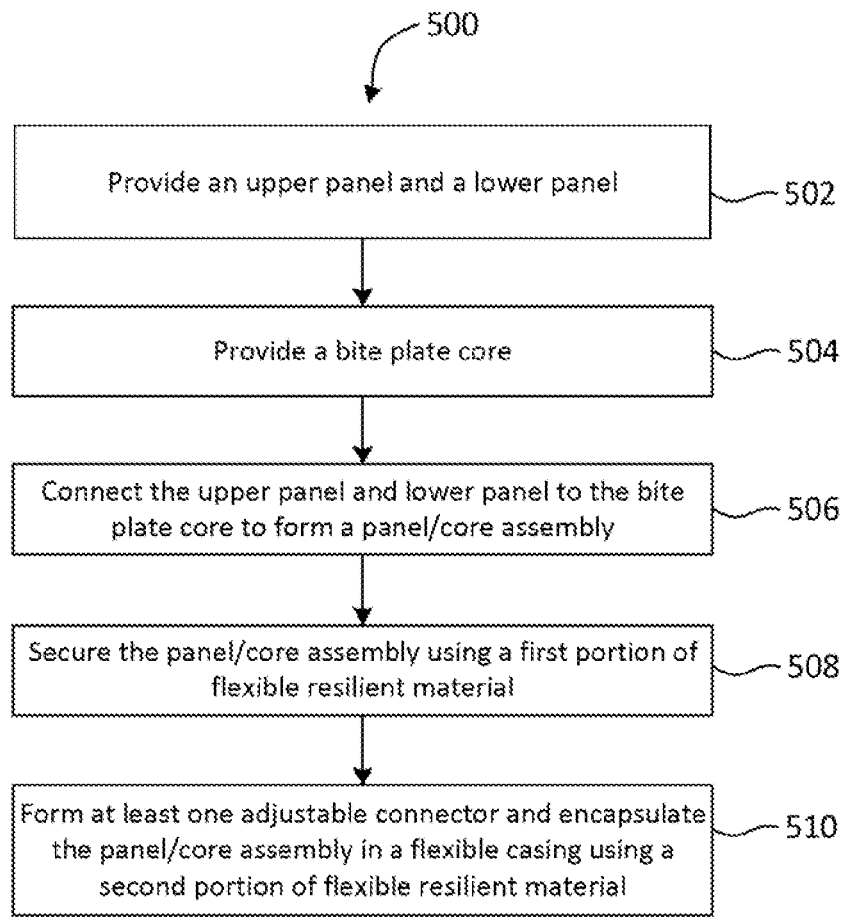
FIG. 15 is a flowchart of another example method for making a mouthpiece apparatus for intraoral therapy, according to some embodiments.

FIG. 15 is a flowchart of another example method 500 for making an adjustable mouthpiece apparatus according to some embodiments. At block 502, an upper panel and a lower panel are provided. Block 502 may have similar steps as block 402 of method 400 as described above.

At block 504, a bite plate core is provided. The bite plate core may be similar in structure to the bite plate core 160 of mouthpiece apparatus 102 as described above.

At block 506, the upper panel and the lower panel are connected to the bite plate core to form a panel/core assembly. In some embodiments, the upper panel is connected to the bite plate core by a first flexible circuit board (FCB). The first FCB may be similar in structure to the first FCB 156 of the mouthpiece apparatus 102 as described above. The lower panel may be connected to an opposed side of the bite plate core by a second FCB. The second FCB may be similar in structure to the second FCB 158 of the mouthpiece 102 as described above. The first and second FCBs may be coupled to the bite plate core using a suitable adhesive or any other suitable coupling means.

At block 508, the panel/core assembly is secured using a first portion of flexible resilient material. In some embodiments, securing the panel/core assembly comprises placing the panel/core assembly into a first mold and injecting the first portion of flexible resilient material into the first mold to form at least one strip of flexible resilient material on and/or around at least a portion of the panel/core assembly to secure the components of the panel/core assembly together and provide the desired position of the panel/core assembly for a second mold, as described in more detail with respect to block 510 below. In some embodiments, a first strip of flexible resilient material may extend from the upper array, along the first FCB, to the bite plate core, thereby securing the upper panel, the first FCB, and the bite plate core together. A second strip of flexible resilient material may extend from the lower array, along the second FCB, to the bite plate core, thereby securing the lower panel, the second FCB, and the bite plate core together. In embodiments in which the upper and lower panels comprise respective arrays of emitting elements, a plurality of strips of flexible resilient material may be formed between and/or around the emitting elements to secure the emitting elements in the arrays.

At block 510, at least one adjustable connector may be formed and the panel/core assembly may be encapsulated in a flexible casing using a second portion of flexible resilient material. In some embodiments, the secured panel/core assembly may be placed into a second mold and the second portion of flexible resilient material may be injected into the second mold to form the adjustable connector(s) and to encapsulate the secured panel/core assembly in the flexible casing. In some embodiments, the flexible casing comprises a first casing portion encapsulating the upper panel, a second casing portion encapsulating the lower panel, and a third casing portion encapsulating the bite plate core. The adjustable connector(s) and flexible casings may therefore be substantially integral with one another in this embodiment.

Various modifications besides those already described are possible without departing from the concepts disclosed herein. Moreover, in interpreting the disclosure, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Although particular embodiments have been shown and described, it will be appreciated by those skilled in the art that various changes and modifications might be made without departing from the scope of the disclosure. The terms and expressions used in the preceding specification have been used herein as terms of description and not of limitation, and there is no intention in the use of such terms and expressions of excluding equivalents of the features shown and described or portions thereof.

The invention claimed is:

1. A mouthpiece apparatus for intraoral therapy comprising:
   an upper panel to be positioned proximate a user's maxillary teeth;
   a lower panel to be positioned proximate the user's mandible teeth, wherein each of the upper panel and the lower panel comprises a respective first end and a respective second end;
   a plurality of adjustable connectors interconnecting the upper panel and the lower panel and adjustable to change a spacing between the upper panel and the lower panel wherein the plurality of adjustable connectors comprise:
      a first S-shaped adjustable connector proximate the first ends of the upper and lower panels;
      a second S-shaped adjustable connector proximate the second ends of the upper and lower panels; and
      a central adjustable connector midway between the first ends and second ends of the upper and lower panels;
   at least one emitting element disposed in at least one of the upper panel and the lower panel; and
   at least one flexible circuit board operatively connected to the at least one emitting element, wherein at least a portion of the at least one flexible circuit board is disposed within the central adjustable connector.

2. The mouthpiece apparatus of claim 1, wherein the plurality of adjustable connectors are compressible and compression of the plurality of adjustable connectors reduces the spacing between the upper panel and the lower panel.

3. The mouthpiece apparatus of claim 1, wherein each of the first S-shaped adjustable connector and the second S-shaped adjustable connector are approximately symmetrical.

4. The mouthpiece apparatus of claim 1, wherein each of the first S-shaped adjustable connector and the second S-shaped adjustable connector comprises: a substantially vertical upper segment extending from the upper panel; a substantially vertical lower segment extending from the lower panel, the lower segment horizontally offset from the upper segment; and a middle segment interconnecting the upper segment and the lower segment.

5. The mouthpiece apparatus of claim 1, further comprising a bite plate between the upper panel and the lower panel.

6. The mouthpiece apparatus of claim 5, wherein the central adjustable connector comprises an upper portion interconnecting the upper panel to the bite plate and a lower portion interconnecting the bite plate to the lower panel.

7. The mouthpiece apparatus of claim 1, wherein at least one adjustable connector of the plurality adjustable connectors comprises a flexible resilient material or a plastically deformable material.

8. The mouthpiece apparatus of claim 1, wherein the at least one emitting element is encapsulated in a flexible casing.

9. The mouthpiece apparatus of claim 8, wherein the flexible casing comprises at least one depression proximate the at least one emitting element.

10. The mouthpiece apparatus of claim 1, wherein the at least one emitting element comprises at least one of an ultrasound emitter, a light emitter, a heat emitter, a vibration emitter, or an electromagnetic field emitter.

11. A system for intraoral therapy comprising:
    the mouthpiece apparatus of claim 1;
    an electronics controller operatively connected to the at least one emitting element to control emissions from the at least one emitting element via the at least one flexible circuit board to control emissions from the at least one emitting element.

12. A method for making a mouthpiece apparatus for intraoral therapy, comprising;
    providing an upper panel and a lower panel, wherein at least one of the upper panel and the lower panel comprises at least one emitting element, and wherein each of the upper panel and the lower panel comprises a respective first end and a respective opposed second end;
    operatively connecting at least one flexible circuit board to the at least one emitting element;
    interconnecting the upper panel and the lower panel with a plurality of adjustable connectors, wherein at least one adjustable connector, of the plurality of adjustable connectors, comprises wherein at least one adjustable connector, of the plurality of adjustable connectors, comprises:
       a first S-shaped adjustable connector proximate the first ends of the upper and lower panels;
       a second S-shaped adjustable connector proximate the second ends of the upper and lower panels, and
       a central adjustable connector midway between the first ends and second ends of the upper and lower panels; and wherein at least a portion of the at least one flexible circuit board is disposed within the central adjustable connector.

13. The method of claim 12, further comprising encapsulating each of the upper panel and the lower panel in a respective flexible casing.

14. The method of claim 12, further comprising providing a bite plate core.

15. The method of claim 14, wherein interconnecting the upper panel and the lower panel comprises:
   connecting the upper panel and the lower panel to the bite plate core to form a panel/core assembly;
   securing the panel/core assembly using a first portion of flexible resilient material; and
   forming the plurality of adjustable connectors and encapsulating the secured panel/core assembly in a flexible casing using a second portion of flexible resilient material.

\* \* \* \* \*